(12) United States Patent
Shimomura et al.

(10) Patent No.: US 10,488,376 B2
(45) Date of Patent: *Nov. 26, 2019

(54) DATA PROCESSING SYSTEM AND PROGRAM FOR CHROMATOGRAPH MASS SPECTROMETER

(71) Applicant: SHIMADZU CORPORATION, Kyoto-shi, Kyoto (JP)

(72) Inventors: Manabu Shimomura, Kyoto (JP); Kaori Tanaka, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 600 days.

This patent is subject to a terminal disclaimer.

(21) Appl. No.: 15/122,445

(22) PCT Filed: Mar. 3, 2014

(86) PCT No.: PCT/JP2014/055288
§ 371 (c)(1),
(2) Date: Aug. 30, 2016

(87) PCT Pub. No.: WO2015/132861
PCT Pub. Date: Sep. 11, 2015

(65) Prior Publication Data
US 2017/0067865 A1 Mar. 9, 2017

(51) Int. Cl.
*G01N 30/86* (2006.01)
*H01J 49/00* (2006.01)
*G01N 30/72* (2006.01)

(52) U.S. Cl.
CPC ..... *G01N 30/8658* (2013.01); *G01N 30/7233* (2013.01); *G01N 30/8631* (2013.01);
(Continued)

(58) Field of Classification Search
CPC .......... G01N 30/8634; G01N 30/8675; G01N 30/88; G01N 30/626; H01J 49/0031; H01J 49/0036; H01J 49/26
See application file for complete search history.

(56) References Cited

U.S. PATENT DOCUMENTS

2004/0084613 A1* 5/2004 Bateman ............. H01J 49/0027
250/281

FOREIGN PATENT DOCUMENTS

JP  2005-77094 A  3/2005
JP  2005077094 A  *  3/2005
(Continued)

OTHER PUBLICATIONS

International Search Report for PCT/JP2014/055288 dated Jun. 3, 2014.
(Continued)

*Primary Examiner* — Michael J Dalbo
(74) *Attorney, Agent, or Firm* — Sughrue Mion, PLLC

(57) ABSTRACT

In a chromatogram mass spectrometer's data processing system, if the intensity of a target peak originating from a target component at a target mass-to-charge ratio is equal to or higher than a threshold, the mass-to-charge ratio of a peak having a signal intensity lower than the threshold on the mass spectrum corresponding to the point in time where the target peak appears is designated as a correction mass-to-charge ratio. A mass spectrum at a point in time in the target peak where the signal intensity does not exceed the threshold is acquired. A sensitivity factor is calculated by dividing the strength at the target mass to-charge ratio on this mass spectrum by the strength at the correction mass to-charge ratio on the same spectrum. A mass chromatogram at the correction mass-to-charge ratio is created. This mass chro-
(Continued)

matogram is multiplied by the sensitivity factor to create a corrected mass chromatogram.

8 Claims, 6 Drawing Sheets

(52) U.S. Cl.
CPC ...... *G01N 30/8675* (2013.01); *H01J 49/0031* (2013.01); *H01J 49/0036* (2013.01)

(56) References Cited

FOREIGN PATENT DOCUMENTS

| JP | 2010-96642 A | 4/2010 | |
|---|---|---|---|
| WO | WO-2012073322 A1 * | 6/2012 | .......... H01J 49/0036 |
| WO | 2013/061466 A1 | 5/2013 | |

OTHER PUBLICATIONS

Written Opinion for PCT/JP2014/055288 dated Jun. 3, 2014. [PCT/ISA/237].

* cited by examiner

FIRST MASS CHROMATOGRAM

MASS SPECTRUM AT TIME t1

MASS SPECTRUM AT TIME t2
(CORRECTION MASS SPECTRUM)

SECOND MASS CHROMATOGRAM

CORRECTED MASS CHROMATOGRAM

DATA PROCESSING SYSTEM AND PROGRAM FOR CHROMATOGRAPH MASS SPECTROMETER

CROSS REFERENCE TO RELATED APPLICATIONS

This application is a National Stage of International Application No. PCT/JP2014/055288 filed Mar. 3, 2014, the contents of which are incorporated herein by refrence in its entirety.

TECHNICAL FIELD

The present invention relates to a data processing system and program for a chromatograph mass spectrometer including a chromatograph (such as a liquid chromatograph or gas chromatograph) coupled with a mass spectrometer.

BACKGROUND ART

In a chromatograph mass spectrometer, three-dimensional data consisting of the three axes of time, mass-to-charge ratio and signal intensity (e.g. output voltage) are collected by temporally separating the components in a sample with the chromatograph and acquiring a mass spectrum with the mass spectrometer by sequentially analyzing each component eluted from the chromatograph (for example, see Patent Literature 1). In a data processing system for a chromatograph mass spectrometer, a peak which appears on such three-dimensional data is detected, and the substance corresponding to that peak is identified from the peak position (retention time and mass-to-charge ratio) with reference to a previously-set identification table. Additionally, a mass chromatogram (i.e. a graph with the horizontal axis representing time and the vertical axis representing the signal intensity at a specific mass-to-charge ratio) related to a mass-to-charge ratio specific to a target component to be quantitatively analyzed is created from the three-dimensional data, and the height or area of the peak located at the retention time of the target component on the mass chromatogram is measured. Then, the concentration or quantity of the target compound is calculated with reference to a calibration curve showing the relationship between the peak-area value and the concentration (content) of the target compound which has been previously created based on the result of a measurement of a standard sample or similar substance.

In general, such a data processing system has limits on the magnitude of the signal that can be processed, due to hardware limitations of the signal-processing circuits including an A/D converter. The system cannot correctly perform calculations if the magnitude of the input signal is higher than the upper limit or lower than the lower limit.

Besides such a limitation related to signal processing, ion detection by a mass spectrometer involves the problem that the reliability of the detection result varies with the level of the signal. For example, if the concentration of the component in the sample is too low, the accuracy of the quantitative determination deteriorates due to the influence of the noise in the detection signal. Conversely, if the component concentration is too high, the non-linearity of the detection signal becomes noticeable, so that the accuracy of the quantitative determination similarly deteriorates. Accordingly, for an analysis using a conventional chromatograph mass spectrometer, the sample needs to be appropriately diluted so that the component concentrations in the sample will be included in a predetermined range (dynamic range).

CITATION LIST

Patent Literature

Patent Literature 1: JP 2010-096642 A ([0002])

SUMMARY OF INVENTION

Technical Problem

In the case where the sample contains a plurality of target components, if the concentrations of those components are not significantly different, the concentration of the sample, the sensitivity of the detector and other parameters only need to be set so that all of the target components will be included in the dynamic range. However, if there is a considerable difference in the concentration among the target components, it is impossible to correctly perform the analysis by any setting, since setting the parameters for correctly detecting the lowest-concentration component (impurity) causes deformation or saturation of the signal of the highest-concentration component (principal component), while setting the parameters for correctly detecting the highest-concentration component (principal component) causes the lowest-concentration component (impurity) to be obscured by noise.

A conventional method for addressing this problem is to perform an analysis on each of a plurality of samples prepared with different concentrations, and correct the obtained results according to their dilution ratios to determine the concentrations (or ratios of concentration) of the target components. However, this method is inefficient since it requires a considerable amount of time for the measurement.

The present invention has been developed in view of the previously described point. Its objective is to provide a data processing system for a chromatograph mass spectrometer capable of the quantitative determination of a target component without being affected by the noise in the detection signal and the non-linearity of the same signal.

Solution To Problem

The data processing system for a chromatograph mass spectrometer according to the first aspect of the present invention developed for solving the previously described problem is a data processing system for a chromatograph mass spectrometer which creates a chromatogram based on a temporal change in a mass spectrum acquired over a mass-to-charge-ratio range including a target mass-to-charge ratio used for the quantitative determination of a target component, the system including:

a) a first mass chromatogram creator for creating a first mass chromatogram which shows a temporal change in the signal intensity at the target mass-to-charge ratio;

b) a correction mass-to-charge ratio designator for determining whether or not the signal intensity at the peak top of a target peak which is a peak corresponding to the target component on the first mass chromatogram is equal to or higher than a predetermined threshold, and for designating, as a correction mass-to-charge ratio, a mass-to-charge ratio of a peak showing a signal intensity lower than the predetermined threshold on a mass spectrum corresponding to the occurrence time of the aforementioned peak top if the signal intensity at the peak top is equal to or higher than the predetermined threshold;

c) a correction mass spectrum acquirer for acquiring a correction mass spectrum which is the mass spectrum at a point in time where the signal intensity does not exceed the threshold within the target peak;

d) a sensitivity factor calculator for calculating a sensitivity factor which is the signal intensity at the target mass-to-charge ratio on the correction mass spectrum divided by the signal intensity at the correction mass-to-charge ratio on the same correction mass spectrum;

e) a second mass chromatogram creator for creating a second mass chromatogram which shows a temporal change in the signal intensity at the correction mass-to-charge ratio; and f) a corrected mass chromatogram creator for creating a corrected mass chromatogram by multiplying the second mass chromatogram by the sensitivity factor.

If a mass chromatogram is created for each of a plurality of kinds of ions having different mass-to-charge ratios which originate from a specific component (compound), a chromatogram peak appears in any of those mass chromatograms at or near the point in time where the component appears (i.e. at the retention time), and those mass chromatogram peaks become similar to each other in shape (as long as neither the distortion nor saturation of the signal occurs). Being "similar to each other in shape" means that the shape of one chromatogram can be obtained by expanding or reducing another chromatogram along the vertical axis (intensity axis). Based on this fact, in the data processing system for a chromatograph mass spectrometer according to the present invention, a "sensitivity factor" is calculated by dividing the signal intensity at the target mass-to-charge ratio on the correction mass spectrum by the signal intensity at the correction mass-to-charge ratio on the same correction mass spectrum, and a corrected mass chromatogram is created by multiplying, by the sensitivity factor, the mass chromatogram related to a mass-to-charge ratio at which an ion originating from the target component is observed with no influence of the distortion or saturation (i.e. the "correction mass-to-charge ratio"). The sensitivity factor corresponds to the ratio of the signal intensity at the target mass-to-charge ratio to the signal intensity at the correction mass-to-charge ratio. Therefore, by multiplying the mass chromatogram acquired at the correction mass-to-charge ratio by the sensitivity factor, the true mass chromatogram (free from the influence of the distortion or saturation) at the target mass-to-charge ratio can be obtained. Accordingly, by using the corrected mass chromatogram in the calculation of the area or height of the peak which appears at or near the retention time of the target component, an accurate quantitative determination result can be obtained.

The data processing system for a chromatograph mass spectrometer according to the second aspect of the present invention developed for solving the previously described problem is a data processing system for a chromatograph mass spectrometer which creates a chromatogram based on a temporal change in a mass spectrum acquired over a mass-to-charge-ratio range including a target mass-to-charge ratio used for the quantitative determination of a target component, the system including:

a) a first mass chromatogram creator for creating a first mass chromatogram which shows a temporal change in the signal intensity at the target mass-to-charge ratio;

b) a correction mass-to-charge ratio designator for determining whether or not the signal intensity at the peak top of a target peak which is a peak corresponding to the target component on the first mass chromatogram is equal to or higher than a predetermined threshold, and for designating, as a correction mass-to-charge ratio, a mass-to-charge ratio of a peak showing a signal intensity lower than the predetermined threshold on a mass spectrum corresponding to the occurrence time of the aforementioned peak top if the signal intensity at the peak top is equal to or higher than the predetermined threshold;

c) a correction mass spectrum acquirer for acquiring a correction mass spectrum which is the mass spectrum at a point in time where the signal intensity does not exceed the threshold within the target peak;

d) a sensitivity factor calculator for calculating a sensitivity factor which is the signal intensity at the target mass-to-charge ratio on the correction mass spectrum divided by the signal intensity at the correction mass-to-charge ratio on the same correction mass spectrum;

e) a second mass chromatogram creator for creating a second mass chromatogram which shows a temporal change in the signal intensity at the correction mass-to-charge ratio;

f) a corresponding peak height/area calculator for calculating the height or area of a corresponding peak which is a peak appearing on the second mass chromatogram and at the same point in time as the target peak; and g) a corrected peak height/area calculator for calculating a corrected peak height or corrected peak area by multiplying the height or area of the corresponding peak by the sensitivity factor.

As noted earlier, the sensitivity factor corresponds to the ratio of the signal intensity at the target mass-to-charge ratio to the signal intensity at the correction mass-to-charge ratio. Therefore, the true peak height or peak area (free from the influence of the distortion or saturation) at the target mass-to-charge ratio (i.e. the corrected peak height or corrected peak area) can be obtained by determining the height or area of the peak ("corresponding peak") which appears at or near the retention time of the target component (i.e. the occurrence time of the target peak) on the mass chromatogram related to the correction mass-to-charge ratio and then multiplying the obtained value by the sensitivity factor.

Advantageous Effects of the Invention

As described thus far, with the data processing system for a chromatograph mass spectrometer according to the first or second aspect of the present invention, even when the mass chromatogram at the target mass-to-charge ratio is distorted or saturated, it is possible to create a true mass chromatogram at the target mass-to-charge ratio or obtain the true peak height or peak area at the target mass-to-charge ratio by using a mass chromatogram at the correction mass-to-charge ratio at which neither the distortion nor saturation is present.

Therefore, even the quantity of a high concentration sample that would need to be diluted in the conventional case can be correctly determined without dilution, so that the amount of labor for the analysis will be reduced. In the case of the measurement of a sample which contains a mixture of a high-concentration principal component and a low-concentration impurity, the concentration of the entire sample can be increased (the dilution ratio can be lowered) so as to enable the analysis of the impurity (or other components). Although increasing the concentration of the entire sample may cause distortion or saturation of the mass chromatogram corresponding to the principal component, the influence of the distortion or saturation can be removed in the previously described manner. Therefore, the data processing can be performed on both the principal component and the impurity (or similar components) by a single analysis using a single detector and without being influenced by the noise (distortion) in the detection signal or non-linearity (saturation) of the same signal.

DESCRIPTION OF EMBODIMENTS

Modes for carrying out the present invention are hereinafter described using embodiments. The following description deals with the case of using a liquid chromatograph as the chromatograph. It should be noted that the description similarly applies in the case of using a gas chromatograph.

Embodiment 1

Figure 1:
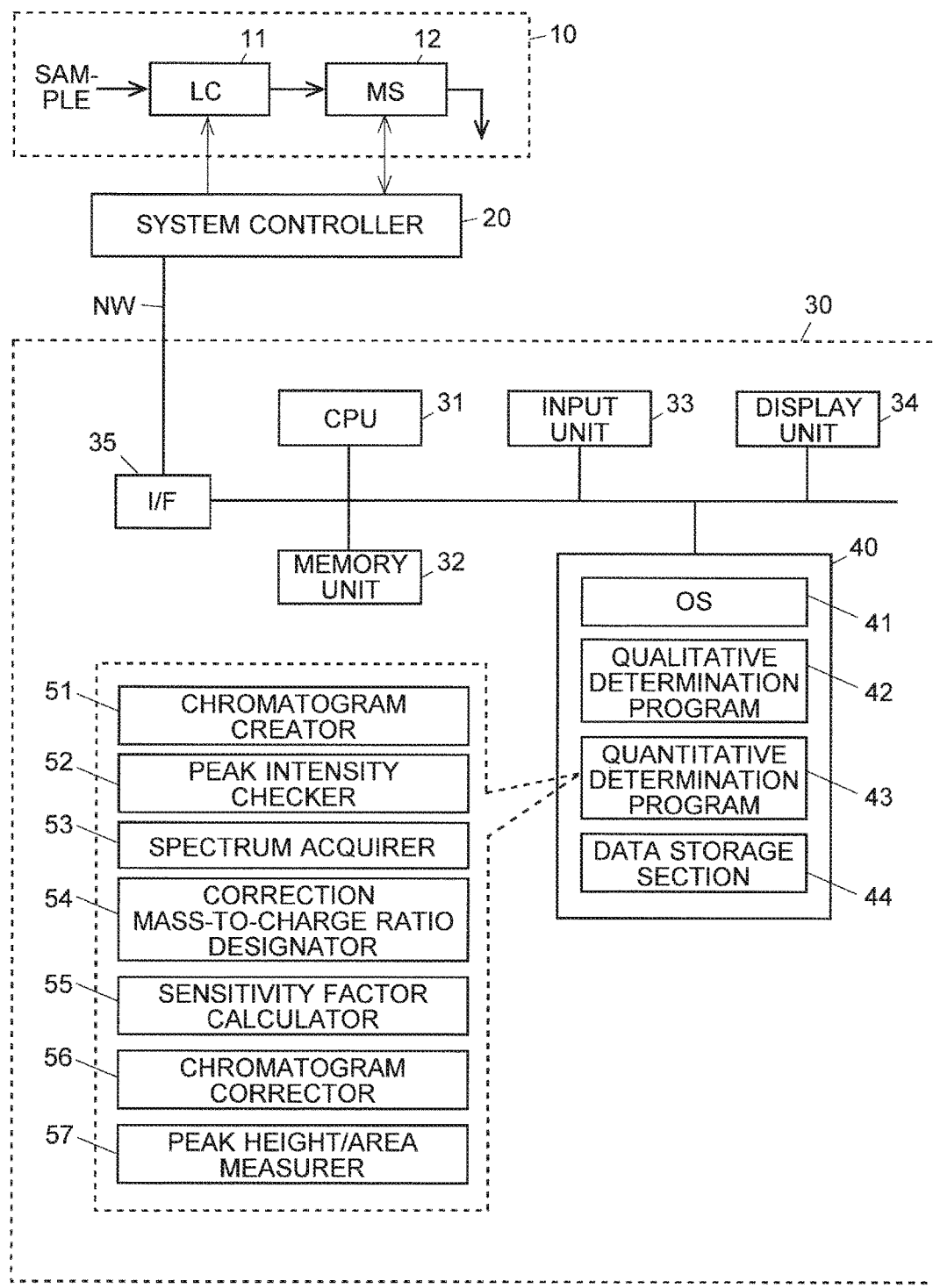
FIG. 1 is a schematic configuration diagram of a sample analyzing system including a data processing system for a chromatograph mass spectrometer according to Embodiment 1.

FIG. 1 is a schematic configuration diagram of a sample analyzing system including a data processing system for a chromatograph mass spectrometer according to the present embodiment. This sample analyzing system is composed of: a liquid chromatograph mass spectrometer (LC-MS) 10 in which a liquid chromatograph (LC) 11 for temporally separating the components contained in a liquid sample is connected to a mass spectrometer (MS) 12 for analyzing each of the separated components within a predetermined mass-to-charge-ratio range; a system controller 20 connected to the LC-MS 10; and a data processing system 30 for processing data fed from the LC-MS 10 via the system controller 20.

The data processing system 30 is actually a computer, such as a workstation or personal computer, including a central processing unit (CPU) 31 with the following units connected to each other: a memory unit 32; an input unit 33 including a keyboard, mouse and/or other devices; a display unit 34, such as a liquid crystal display (LCD); and a storage unit 40 including a mass storage device, such as a hard disk drive and/or solid state drive. In the storage unit 40, an operating system (OS) 41, qualitative determination program 42, and qualitative determination program 43 (which is the program according to the present invention) are stored, as well as a data storage section 44 is provided. Furthermore, the data processing system 30 is provided with an interface (I/F) 35 for controlling a direct connection with an external device or a network connection with an external device (or other devices) through the local area network (LAN) or the like. Through this interface 35, the data processing system 30 is connected to the system controller 20 via the network cable NW (or wireless LAN).

In FIG. 1, a chromatogram creator 51, peak intensity checker 52, spectrum acquirer 53, correction mass-to-charge ratio designator 54, sensitivity factor calculator 55, chromatogram corrector 56, and peak height/area measurer 57 are shown in relation to the quantitative determination program 43. Basically, all of them are functional means realized in the form of software by the CPU 31 executing the quantitative determination program 43. The quantitative determination program 43 does not need to be an independent program. There is no specific limitation on its form; for example, it may be a built-in function included in a program for controlling the LC-MS 10.

In a sample analysis by the sample analyzing system of the present embodiment, the components in the sample are temporally separated by the LC 11. For the eluate supplied from the LC 11, the MS 12 repeatedly performs a scan measurement over a previously-set range of mass-to-charge ratios in a fixed cycle of time. The detection signals produced by the MS 12 are sequentially sent through the system controller 20 to the data processing system 30 and stored in the data storage section 44. In this manner, three-dimensional data consisting of the three axes of time, mass-to-charge ratio and signal intensity are stored in the data storage section 44 as the analysis result on the sample.

The qualitative determination program 42 detects a peak appearing on the three-dimensional data and identifies the substance corresponding to that peak from the peak position (retention time and mass-to-charge ratio) with reference to an identification table previously stored in the storage unit 40.

Figure 2:
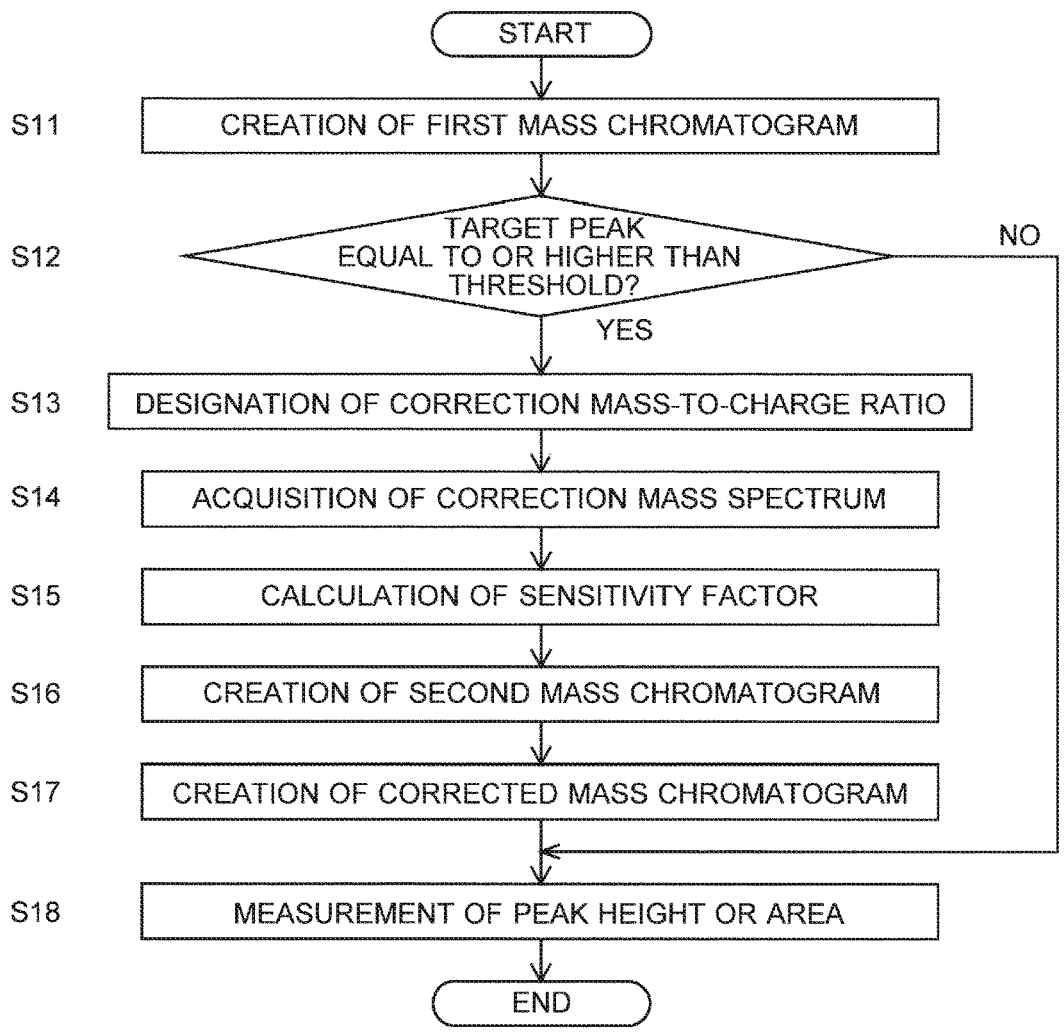
FIG. 2 is a flowchart showing the process steps by a quantitative determination program in the same embodiment.

Subsequently, based on the three-dimensional data, the quantitative determination program 43 calculates the concentration or quantity of the component in the sample identified by the qualitative determination program 42. The process performed by the quantitative determination program 43 for this calculation is hereinafter described with reference to the flowchart of FIG. 2.

Initially, the chromatogram creator 51 in the quantitative determination program 43 creates a mass chromatogram related to the target mass-to-charge ratio M1, which is previously determined as the mass-to-charge ratio to be used for the quantitative determination of the target component, by extracting measurement data related to the target mass-to-charge ratio M1 from the three-dimensional data (Step S11). This mass chromatogram is hereinafter called the "first mass chromatogram". The target mass-to-charge ratio M1 may be previously set by an operator using the input unit 33, or the mass-to-charge ratio to be used for the quantitative determination of each compound may be previously described in the identification table, in which case the system can be configured to read the value of the mass-to-charge ratio corresponding to the compound which is the target component from the identification table, and to automatically set that value as the target mass-to-charge ratio M1.

Subsequently, the peak intensity checker 52 determines whether or not the peak-top value of the peak corresponding to the target component on the first mass chromatogram (target peak) is equal to or higher than the threshold $I_T$ (Step S12). The threshold $I_T$, which is previously stored in the storage unit 40, is set at the highest possible level within the range where the detection signal is free from the influence of the non-linearity (within a range where neither the distortion nor saturation of the detection signal occurs). If the value of the target peak is less than the threshold $I_T$, the detection signal is free from the influence of the non-linearity, so that a correct quantitative value can be obtained from the height or area of the peak on the first mass chromatogram even without the chromatogram correction process (which will be described later). Therefore, in the present case, the operation proceeds to Step S18, where the height or area of the target peak on the first mass chromatogram is measured by the peak height/area measurer 57 (Step S18).

Figure 3:
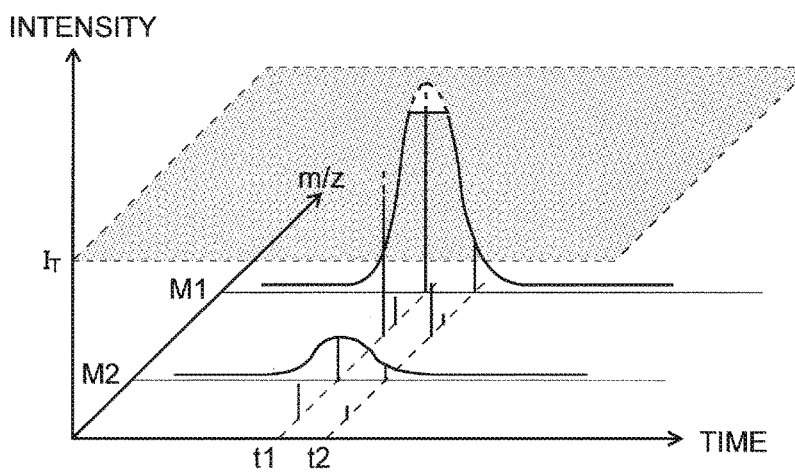
FIG. 3 is a model diagram showing the three-dimensional data obtained through an analysis using an LC-MS.
Figure 4:
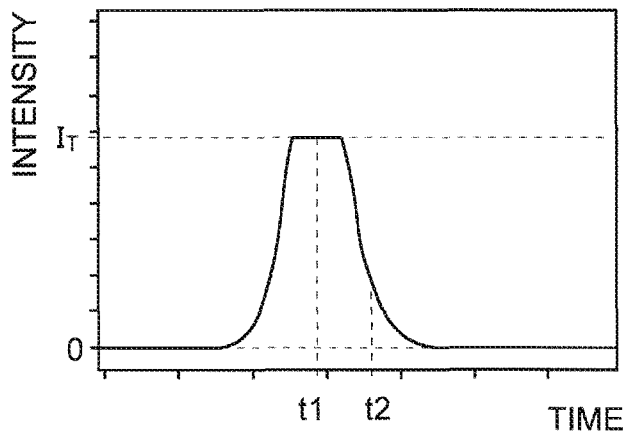
FIG. 4 is a diagram showing one example of the first mass chromatogram.

On the other hand, if the value of the target peak is equal to or greater than the threshold $I_T$, the detection signal is under the influence of the non-linearity, so that it is impossible to obtain the correct quantitative value from the height or area of the peak on the first mass chromatogram. For example, in the case of the three-dimensional data shown in FIG. 3, a chromatogram as shown in FIG. 4 is obtained as the mass chromatogram at the target mass-to-charge ratio M1 (i.e. the first mass chromatogram). In this chromatogram, since the value of the target peak exceeds the threshold $I_T$, the waveform around the peak top is distorted due to the saturation. Therefore, neither the height nor area of the target peak correctly reflects the concentration of the target component in the sample. In such a case, the quantitative determination program 43 in the present embodiment performs the correction process according to Steps S13-S17 to create a chromatogram that is free from the influence of the distortion or saturation at the target mass-to-charge ratio M1 (corrected mass chromatogram).

Figure 5:
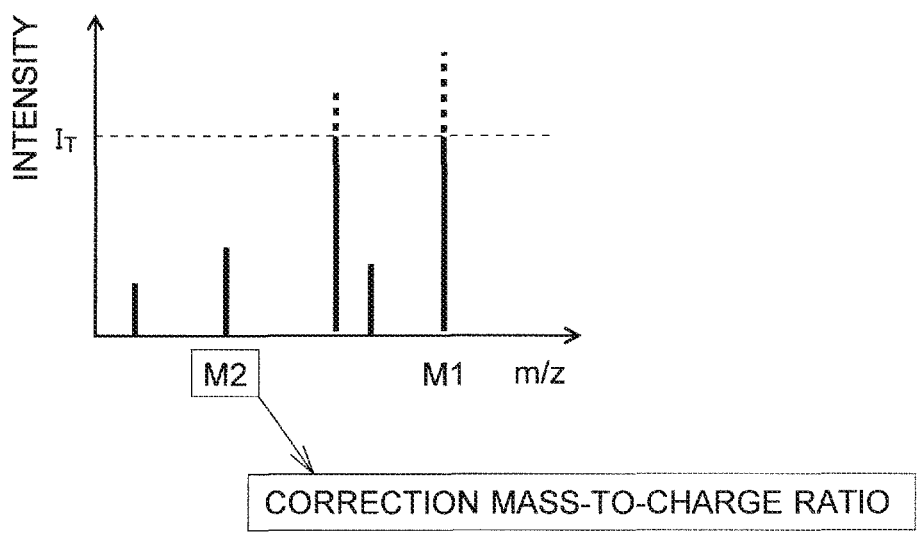
FIG. 5 is a diagram illustrating the method for designating the correction mass-to-charge ratio.

To this end, the spectrum acquirer 53 initially extracts the mass spectrum at the retention time t1 of the target component (i.e. the point in time which corresponds to the peak top of the target peak in the first mass chromatogram) from the three-dimensional data. As a result, a mass spectrum as shown in FIG. 5 is obtained. Subsequently, the correction mass-to-charge ratio designator 54 searches for a peak having the highest signal intensity on this mass spectrum among the peaks which are lower than the threshold $I_T$, and designates the mass-to-charge ratio of this peak as the correction mass-to-charge ratio M2 (Step S13).

Figure 6:
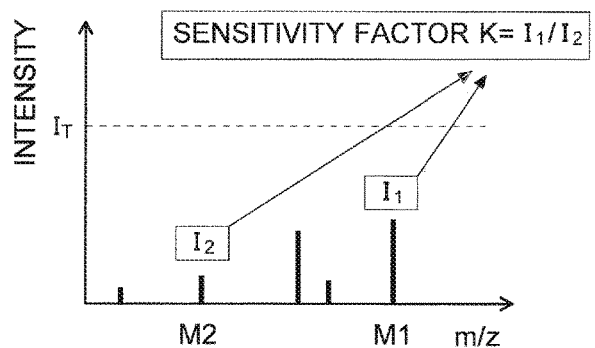
FIG. 6 is a diagram showing one example of the correction mass spectrum.

After that, the spectrum acquirer 53 extracts, from the three-dimensional data, the mass spectrum at time t2 where the signal intensity does not exceed the threshold $I_T$ (e.g. a point in time which belongs to the skirt portion of the peak) in the target peak on the first mass spectrum (Step S14). This mass spectrum is hereinafter called the "correction mass spectrum". One example of the correction mass spectrum is shown in FIG. 6.

Subsequently, the sensitivity factor calculator 55 calculates the sensitivity factor K by dividing the signal intensity $I_1$ at the target mass-to-charge ratio M1 on the correction mass spectrum by the signal intensity $I_2$ at the correction mass-to-charge ratio M2 on the same correction mass spectrum (Step S15).

Figure 7:
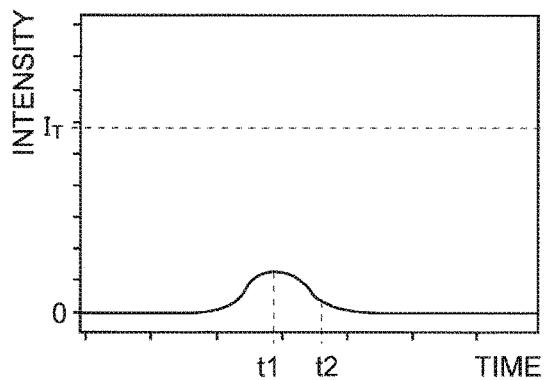
FIG. 7 is a diagram showing one example of the second mass chromatogram.

Next, the chromatogram creator 51 creates a mass chromatogram related to the correction mass-to-charge ratio M2 based on the three-dimensional data (Step S16). This mass chromatogram is hereinafter called the "second mass chromatogram". One example of the second mass chromatogram is shown in FIG. 7. Since the second mass chromatogram is created for a mass-to-charge ratio which originates from the same component as the first mass chromatogram (i.e. the target component), the second mass chromatogram has a peak at or near the retention time t1 of the target component, and its peak shape is similar to the peak shape which would be observed if there was neither the distortion or saturation of the signal at the target mass-to-charge ratio M1.

Figure 8:
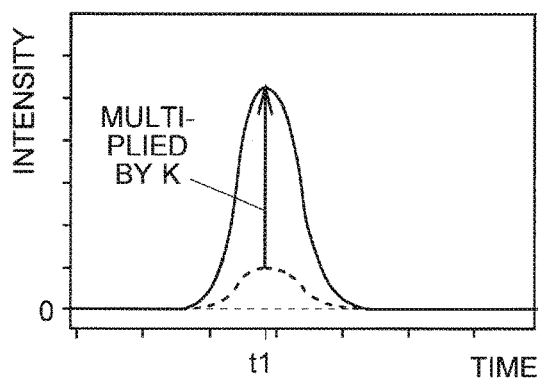
FIG. 8 is a diagram showing one example of the corrected mass spectrum.

The chromatogram corrector 56 creates a corrected mass chromatogram by multiplying this second mass chromatogram by the aforementioned sensitivity factor K (Step S17). One example of the corrected mass chromatogram is shown in FIG. 8. Since the sensitivity factor K corresponds to the ratio of the signal intensity at the target mass-to-charge ratio M1 to the signal intensity at the correction mass-to-charge ratio M2 ($I_1/I_2$), the corrected mass chromatogram obtained by multiplying the second mass chromatogram (the mass chromatogram related to the correction mass-to-charge ratio M2) by the sensitivity factor K becomes the true mass chromatogram (free from the influence of the distortion or saturation) at the target mass-to-charge ratio M1.

Subsequently, the peak height/area measurer 57 measures the height or area of the peak which appears at or near the retention time t1 of the target component on the corrected mass chromatogram (Step S18). As already explained, the corrected mass chromatogram is a mass chromatogram that is free from the influence of the distortion or saturation of the signal. Therefore, the height and area of the peak determined from this mass chromatogram correctly reflect the concentration of the target component in the sample.

In the case of performing a quantitative determination for a plurality of target components in the sample, the processes of Steps S11-S18 are repeated the same number of times as the target components. Even if the plurality of kinds of target components have significantly different concentrations, the sample analyzing system according to the present embodiment does not require the conventional task of diluting the sample to different concentrations before the analysis using the LC-MS is performed. Therefore, the amount of time and labor for the measurement will be reduced.

Embodiment 2

Figure 9:
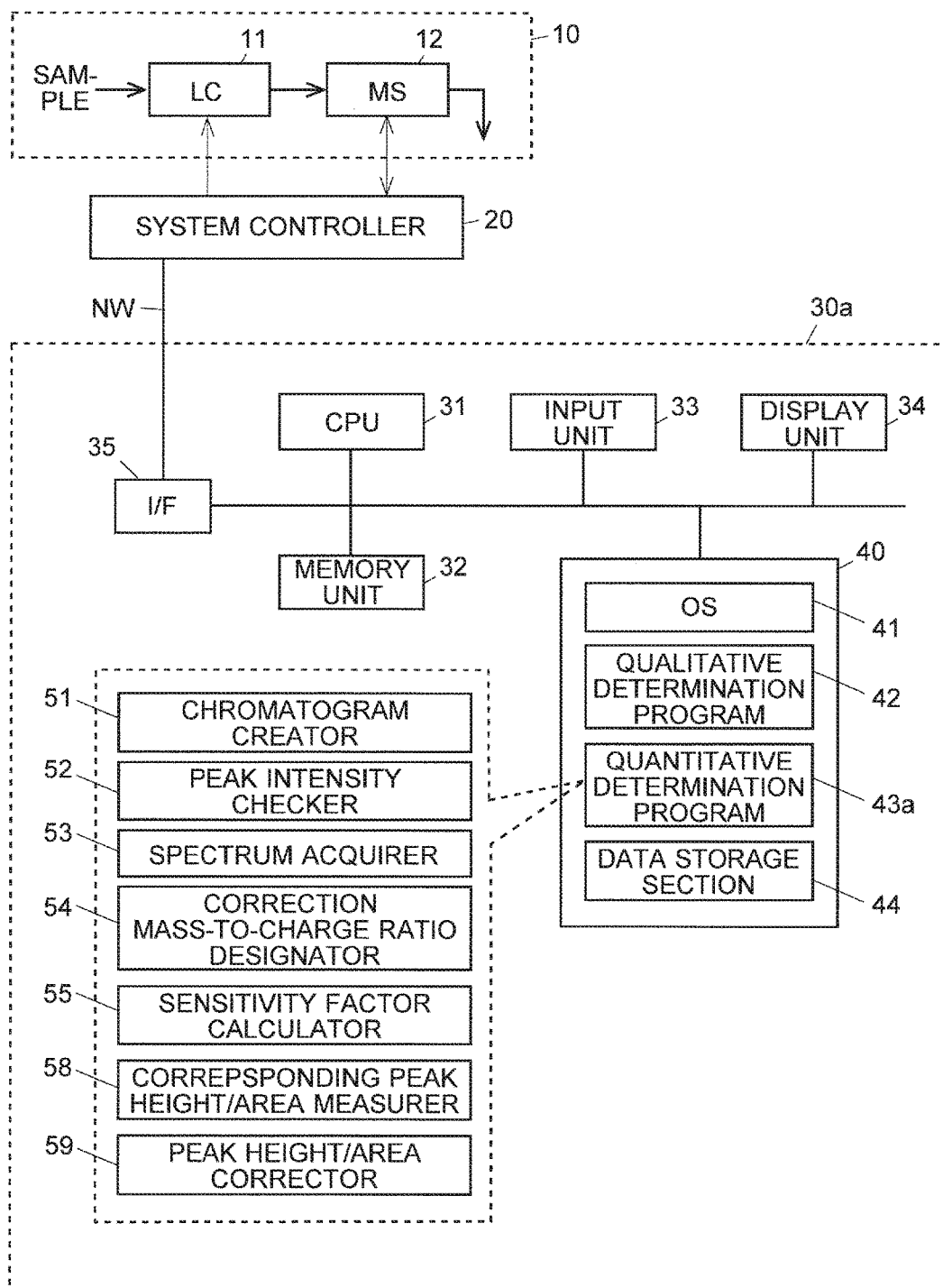
FIG. 9 is a schematic configuration diagram of a sample analyzing system including a data processing system for a chromatograph mass spectrometer according to Embodiment 2.
Figure 10:
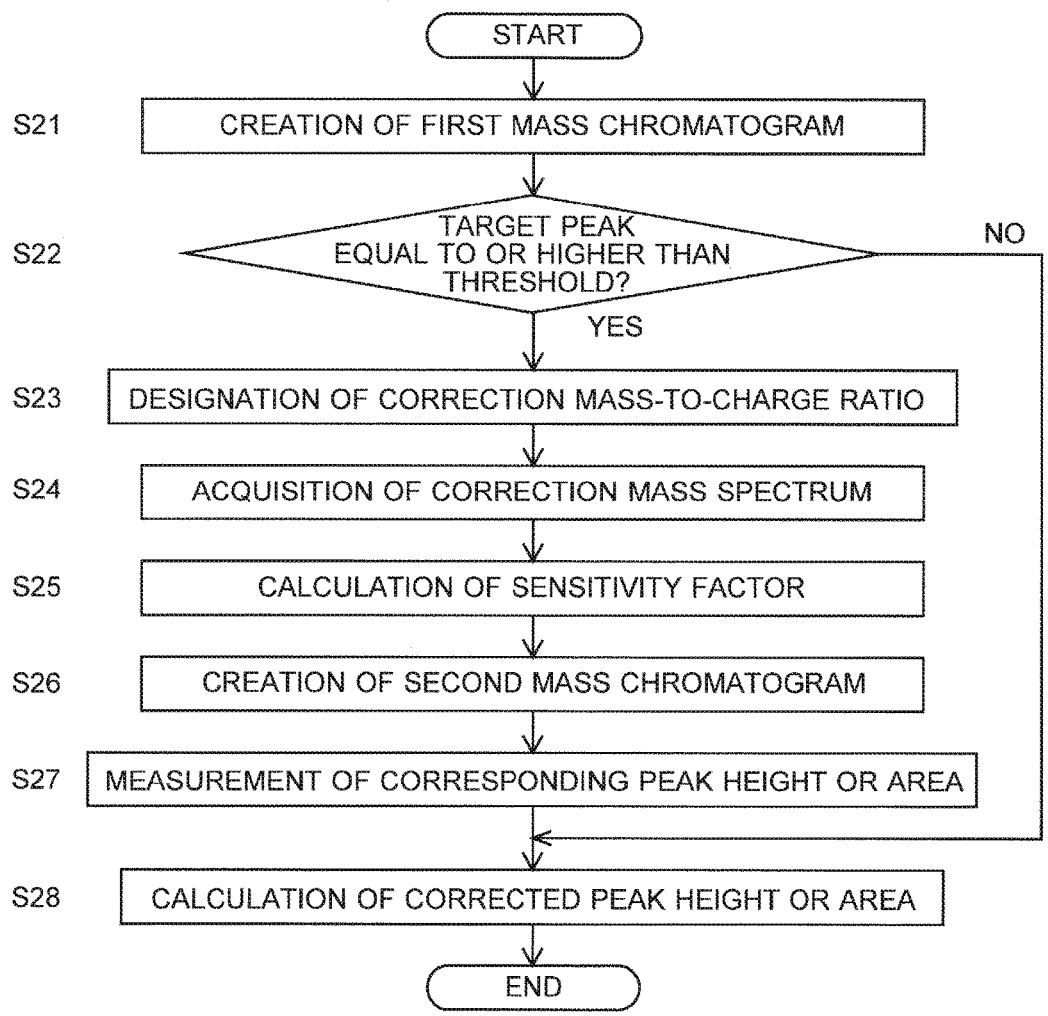
FIG. 10 is a flowchart showing the process steps by a quantitative determination program in the same embodiment.

The second embodiment of the present invention is hereinafter described with reference to FIGS. 9 and 10. FIG. 9 is a schematic configuration diagram of a sample analyzing system including a data processing system 30a for a chromatograph mass spectrometer according to the present embodiment. The sample analyzing system according to the present embodiment is identical to the system of Embodiment 1 except that a corresponding peak height/area measurer 58 and a peak height/area corrector 59 are provided as the functional blocks of the quantitative determination program 43a in place of the previously described chromatogram corrector 56 and the peak height/area measurer 57 (hereinafter, the components that are common to both the present embodiment and Embodiment 1 are denoted by the same numerals, and the descriptions of those components will be appropriately omitted).

In the sample analyzing system according to the previously described Embodiment 1, the true mass chromatogram (free from the influence of the distortion or saturation) at the target mass-to-charge ratio M1 (corrected mass chromatogram) is created by correcting the mass chromatogram at the correction mass-to-charge ratio M2 (second mass chromatogram), and the height or area of the peak is subsequently measured based on the corrected mass chromatogram. By comparison, in the sample analyzing system according to the present embodiment, the height or area of the peak is initially measured based on the mass chromatogram at the correction mass-to-charge ratio M2 (second mass chromatogram), and the thereby obtained value is corrected to calculate the true height or area of the peak at the target mass-to-charge ratio M1. Hereinafter, the process performed by the quantitative determination program 43a in the present embodiment is described with reference to the flowchart of FIG. 10.

Initially, the creation of the first mass chromatogram (Step S21), determination of whether or not the intensity of the target peak is equal to or higher than the threshold (Step S22), designation of the correction mass-to-charge ratio (Step S23), acquisition of the correction mass spectrum (Step S24), calculation of the sensitivity factor (Step S25), and creation of the second mass chromatogram (Step S26) are performed similarly to Steps S11-S16 in Embodiment 1,.

After that, the corresponding peak height/area measurer 58 measures the height or area of the peak located at or near the retention time t1 of the target component ("corresponding peak") on the second mass chromatogram created in Step S26 (Step S27).

Subsequently, the peak height/area corrector 59 calculates the corrected peak height/area by multiplying the measured value obtained in Step S27 by the sensitivity factor K calculated in Step S25 (Step S28). Since the sensitivity factor K corresponds to the ratio of the signal intensity at the target mass-to-charge ratio M1 to the signal intensity at the correction mass-to-charge ratio M2 ($I_1/I_2$), the true height or area of the peak (free from the influence of the distortion or saturation) at the target mass-to-charge ratio M1 can be obtained by multiplying, by the sensitivity factor, the measured value of the height or area of the peak located on the mass chromatogram at the correction mass-to-charge ratio M2 (second mass chromatogram) in the previously described manner.

Thus far, the modes for carrying out the present invention have been described using the embodiments. It should be noted that the present invention is not limited to the previous embodiments, but appropriate changes are permitted within the spirit of the present invention. For example, in the descriptions of Embodiments 1 and 2, it is assumed that the processes of Steps S11-S18 or S21-S28 are performed after the sample measurement by the LC-MS 10 is completed. However, it is also possible to perform a portion or the entirety of the processes in those steps concurrently with the sample measurement by the LC-MS 10.

In Embodiments 1 and 2, the mass-to-charge ratio of a peak showing the highest signal intensity among the peaks lower than the threshold $I_T$ on the mass spectrum at the retention time t1 of the target component is designated as the correction mass-to-charge ratio. However, the method of determining the correction mass-to-charge ratio is not limited to this one. For example, the peaks whose signal intensities are lower than the threshold $I_T$ on the aforementioned mass spectrum may be displayed on the display unit 34 so as to allow users to select an appropriate peak using the input unit 33, or the system may be configured to automatically select a peak which satisfies predefined criteria from among the peaks which do not exceed the threshold $I_T$ and yet are higher than the minimum level of the signal intensity that is distinguishable from noise signals.

REFERENCE SIGNS LIST

10 . . . Liquid Chromatograph Mass Spectrometer (LC-MS)
11 . . . Liquid Chromatograph (LC)
12 . . . Mass Spectrometer (MS)
20 . . . System Controller
30, 30a . . . Data Processing System
31 . . . CPU
32 . . . Memory Unit
33 . . . Input Unit
34 . . . Display Unit
35 . . . Interface
40 . . . Storage Unit
41 . . . OS
42 . . . Qualitative Determination Program
43, 43a . . . Quantitative Determination Program
44 . . . Data Storage Section
51 . . . Chromatogram Creator
52 . . . Peak Intensity Checker
53 . . . Spectrum Acquirer
54 . . . Correction Mass-to-Charge Ratio Designator
55 . . . Sensitivity Factor Calculator
56 . . . Chromatogram Corrector
57 . . . Peak Height/Area Measurer
58 . . . Corresponding Peak Height/Area Measurer
59 . . . Peak Height/Area Corrector

The invention claimed is:

1. A data processing system for a chromatograph mass spectrometer which creates a chromatogram based on a temporal change in a mass spectrum acquired over a mass-to-charge-ratio range including a target mass-to-charge ratio used for a quantitative determination of a target component, the system comprising:
   a) a first mass chromatogram creator for creating a first mass chromatogram which shows a temporal change in a signal intensity at the target mass-to-charge ratio;
   b) a correction mass-to-charge ratio designator for determining whether or not the signal intensity at a peak top of a target peak which is a peak corresponding to the target component on the first mass chromatogram is equal to or higher than a predetermined threshold, and for designating, as a correction mass-to-charge ratio, a mass-to-charge ratio of a peak showing a signal intensity lower than the predetermined threshold on a mass spectrum corresponding to an occurrence time of the aforementioned peak top if the signal intensity at the peak top is equal to or higher than the predetermined threshold;
   c) a correction mass spectrum acquirer for acquiring a correction mass spectrum which is the mass spectrum at a point in time where the signal intensity does not exceed the threshold within the target peak;
   d) a sensitivity factor calculator for calculating a sensitivity factor which is the signal intensity at the target mass-to-charge ratio on the correction mass spectrum divided by the signal intensity at the correction mass-to-charge ratio on the same correction mass spectrum;
   e) a second mass chromatogram creator for creating a second mass chromatogram which shows a temporal change in the signal intensity at the correction mass-to-charge ratio; and
   f) a corrected mass chromatogram creator for creating a corrected mass chromatogram by multiplying the second mass chromatogram by the sensitivity factor.

2. The data processing system for a chromatograph mass spectrometer according to claim 1, wherein the correction mass-to-charge ratio designator designates, as the correction mass-to-charge ratio, a mass-to-charge ratio of a peak showing a highest signal intensity among peaks whose signal intensities are lower than the threshold.

3. A data processing system for a chromatograph mass spectrometer which creates a chromatogram based on a temporal change in a mass spectrum acquired over a mass-to-charge-ratio range including a target mass-to-charge ratio used for a quantitative determination of a target component, the system comprising:

a) a first mass chromatogram creator for creating a first mass chromatogram which shows a temporal change in a signal intensity at the target mass-to-charge ratio;

b) a correction mass-to-charge ratio designator for determining whether or not the signal intensity at a peak top of a target peak which is a peak corresponding to the target component on the first mass chromatogram is equal to or higher than a predetermined threshold, and for designating, as a correction mass-to-charge ratio, a mass-to-charge ratio of a peak showing a signal intensity lower than the predetermined threshold on a mass spectrum corresponding to an occurrence time of the aforementioned peak top if the signal intensity at the peak top is equal to or higher than the predetermined threshold;

c) a correction mass spectrum acquirer for acquiring a correction mass spectrum which is the mass spectrum at a point in time where the signal intensity does not exceed the threshold within the target peak;

d) a sensitivity factor calculator for calculating a sensitivity factor which is the signal intensity at the target mass-to-charge ratio on the correction mass spectrum divided by the signal intensity at the correction mass-to-charge ratio on the same correction mass spectrum;

e) a second mass chromatogram creator for creating a second mass chromatogram which shows a temporal change in the signal intensity at the correction mass-to-charge ratio;

f) a corresponding peak height/area calculator for calculating a height or area of a corresponding peak which is a peak appearing on the second mass chromatogram and at a same point in time as the target peak; and g) a corrected peak height/area calculator for calculating a corrected peak height or corrected peak area by multiplying the height or area of the corresponding peak by the sensitivity factor.

4. The data processing system for a chromatograph mass spectrometer according to claim 3, wherein the correction mass-to-charge ratio designator designates, as the correction mass-to-charge ratio, a mass-to-charge ratio of a peak showing a highest signal intensity among peaks whose signal intensities are lower than the threshold.

5. A non-transitory computer readable medium recording a program for a data processing system for a chromatogram mass spectrometer which creates a chromatogram based on a temporal change in a mass spectrum acquired over a mass-to-charge-ratio range including a target mass-to-charge ratio used for a quantitative determination of a target component, the program making a computer function as:

a) a first mass chromatogram creator for creating a first mass chromatogram which shows a temporal change in a signal intensity at the target mass-to-charge ratio;

b) a correction mass-to-charge ratio designator for determining whether or not the signal intensity at a peak top of a target peak which is a peak corresponding to the target component on the first mass chromatogram is equal to or higher than a predetermined threshold, and for designating, as a correction mass-to-charge ratio, a mass-to-charge ratio of a peak showing a signal intensity lower than the predetermined threshold on a mass spectrum corresponding to an occurrence time of the aforementioned peak top if the signal intensity at the peak top is equal to or higher than the predetermined threshold;

c) a correction mass spectrum acquirer for acquiring a correction mass spectrum which is the mass spectrum at a point in time where the signal intensity does not exceed the threshold within the target peak;

d) a sensitivity factor calculator for calculating a sensitivity factor which is the signal intensity at the target mass-to-charge ratio on the correction mass spectrum divided by the signal intensity at the correction mass-to-charge ratio on the same correction mass spectrum;

e) a second mass chromatogram creator for creating a second mass chromatogram which shows a temporal change in the signal intensity at the correction mass-to-charge ratio; and f) a corrected mass chromatogram creator for creating a corrected mass chromatogram by multiplying the second mass chromatogram by the sensitivity factor.

6. The non-transitory computer readable medium recording a program according to claim 5, wherein the correction mass-to-charge ratio designator designates, as the correction mass-to-charge ratio, a mass-to-charge ratio of a peak showing a highest signal intensity among peaks whose signal intensities are lower than the threshold.

7. A non-transitory computer readable medium recording a program for a data processing system for a chromatogram mass spectrometer which creates a chromatogram based on a temporal change in a mass spectrum acquired over a mass-to-charge-ratio range including a target mass-to-charge ratio used for a quantitative determination of a target component, the program making a computer function as:

a) a first mass chromatogram creator for creating a first mass chromatogram which shows a temporal change in a signal intensity at the target mass-to-charge ratio;

b) a correction mass-to-charge ratio designator for determining whether or not the signal intensity at a peak top of a target peak which is a peak corresponding to the target component on the first mass chromatogram is equal to or higher than a predetermined threshold, and for designating, as a correction mass-to-charge ratio, a mass-to-charge ratio of a peak showing a signal intensity lower than the predetermined threshold on a mass spectrum corresponding to an occurrence time of the aforementioned peak top if the signal intensity at the peak top is equal to or higher than the predetermined threshold;

c) a correction mass spectrum acquirer for acquiring a correction mass spectrum which is the mass spectrum at a point in time where the signal intensity does not exceed the threshold within the target peak;

d) a sensitivity factor calculator for calculating a sensitivity factor which is the signal intensity at the target mass-to-charge ratio on the correction mass spectrum divided by the signal intensity at the correction mass-to-charge ratio on the same correction mass spectrum;

e) a second mass chromatogram creator for creating a second mass chromatogram which shows a temporal change in the signal intensity at the correction mass-to-charge ratio;

f) a corresponding peak height/area calculator for calculating a height or area of a corresponding peak which is a peak appearing on the second mass chromatogram and at a same point in time as the target peak; and g) a corrected peak height/area calculator for calculating a corrected peak height or corrected peak area by multiplying the height or area of the corresponding peak by the sensitivity factor.

8. The non-transitory computer readable medium recording a program according to claim 7, wherein the correction mass-to-charge ratio designator designates, as the correction mass-to-charge ratio, a mass-to-charge ratio of a peak showing a highest signal intensity among peaks whose signal intensities are lower than the threshold.

* * * * *